(12) United States Patent
Bodner

(10) Patent No.: US 11,992,642 B2
(45) Date of Patent: May 28, 2024

(54) IMPLANTABLE MEDICAL DEVICE FOR DELIVERY OF PHARMACOLOGICAL AGENTS TO THE DEEP BRAIN STRUCTURES

(71) Applicant: Medtronic, Inc., Minneapolis, MN (US)

(72) Inventor: Jeffrey Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 17/085,360

(22) Filed: Oct. 30, 2020

(65) Prior Publication Data
US 2022/0134076 A1     May 5, 2022

(51) Int. Cl.
*A61M 39/02*     (2006.01)
(52) U.S. Cl.
CPC ... *A61M 39/0247* (2013.01); *A61M 2039/027* (2013.01); *A61M 2039/0273* (2013.01); *A61M 2039/0276* (2013.01); *A61M 2039/0282* (2013.01); *A61M 2210/1003* (2013.01)
(58) Field of Classification Search
CPC ........ A61M 39/0247; A61M 2039/027; A61M 2039/0273; A61M 2039/0276; A61M 2039/0282; A61M 2210/1003; A61M 5/14276; A61M 2206/20; A61M 2210/0693; A61M 27/006;
(Continued)

(56) References Cited

U.S. PATENT DOCUMENTS

| 5,045,064 A | 9/1991 | Idriss |
| 5,085,644 A | 2/1992 | Watson et al. |
| 5,281,210 A | 1/1994 | Burke et al. |

(Continued)

FOREIGN PATENT DOCUMENTS

| WO | WO0066204 A1 | 11/2000 |
| WO | WO2009129474 A1 | 10/2009 |

(Continued)

OTHER PUBLICATIONS

Alcyone Lifesciences, Inc., Bringing Hope to Spinal Muscular Atrophy (SMA) Patients with the Alcyone Lifesciences ThecaFlex DRx™ System Breakthrough Device, Dec. 2, 2019, 3 pages, available at: https://www.prnewswire.com/news-releases/bringing-hope-to-spinal-muscular-atrophy-sma-patients-with-the-alcyone-lifesciences-thecaflex-drx-system-breakthrough-device-300967222.html.

*Primary Examiner* — Lauren P Farrar
*Assistant Examiner* — Kathleen Paige Farrell
(74) *Attorney, Agent, or Firm* — Husch Blackwell LLP

(57) ABSTRACT

An intrathecal drug delivery system includes: an intrathecal drug delivery device configured to deliver a fluid containing one or more pharmaceutical agents intrathecally to the cerebrospinal fluid (CSF) within a spinal canal of a patient and a deep brain catheter having an elongated body, extending from a distal end implanted within a deep brain structure of a patient and a proximal end positioned within the subarachnoid space directly adjacent to the brain to provide a passageway, via an inner lumen, between the subarachnoid space and the deep brain structure. The drug delivery system is configured to transport the pharmaceutical agent(s), using diffusion and the pulsatile flow of the CSF, through the deep brain catheter from the subarachnoid space to the deep brain structure.

20 Claims, 6 Drawing Sheets

(58) Field of Classification Search
CPC ...... A61M 2202/0464; A61M 25/0194; A61M 39/0208
See application file for complete search history.

(56) References Cited

U.S. PATENT DOCUMENTS

| | | | |
|---|---|---|---|
| 5,527,307 A | 6/1996 | Srisathapat et al. |
| 5,702,372 A | 12/1997 | Nelson |
| 5,833,654 A | 11/1998 | Powers et al. |
| 5,957,890 A | 9/1999 | Mann et al. |
| 6,013,051 A | 1/2000 | Nelson |
| 6,042,579 A | 3/2000 | Elsberry et al. |
| 6,572,583 B1 | 6/2003 | Olsen et al. |
| 6,852,106 B2 | 2/2005 | Watson et al. |
| 6,962,577 B2 | 11/2005 | Tallarida et al. |
| 7,351,239 B2 | 4/2008 | Gill |
| 7,366,562 B2 | 4/2008 | Dukesherer et al. |
| 7,637,897 B2 | 12/2009 | Ginggen |
| 7,803,143 B2 | 10/2010 | Tallarida et al. |
| 7,963,956 B2 | 6/2011 | Kunst |
| 8,320,991 B2 | 11/2012 | Jascob et al. |
| 8,419,710 B2 | 4/2013 | Keimel et al. |
| 8,483,802 B2 | 7/2013 | Kalpin et al. |
| 8,545,484 B2 | 10/2013 | Haase et al. |
| 8,591,456 B2 | 11/2013 | Steinbach |
| 8,613,724 B2 | 12/2013 | Lanier, Jr. et al. |
| 8,721,605 B2 | 5/2014 | Brandt et al. |
| 8,915,893 B2 | 12/2014 | Steinbach |
| 8,932,271 B2 | 1/2015 | Hamatake et al. |
| 9,079,004 B2 | 7/2015 | Wiley et al. |
| 9,427,553 B2 | 8/2016 | Nelson |
| 9,433,764 B2 | 9/2016 | East et al. |
| 9,744,338 B2 | 8/2017 | East et al. |
| 9,782,536 B2 | 10/2017 | Skutnik et al. |
| 9,919,102 B2 | 3/2018 | John |
| 9,981,117 B2 | 5/2018 | Brandt et al. |
| 9,993,600 B2 | 6/2018 | Lanier, Jr. et al. |
| 10,238,851 B2 | 3/2019 | Butziger et al. |
| 10,376,635 B2 | 8/2019 | Haase |
| 10,589,024 B2 | 3/2020 | John |
| 10,596,362 B2 | 3/2020 | Fielder et al. |
| 10,625,060 B2 | 4/2020 | Børgesen |
| 11,400,255 B1 * | 8/2022 | Chou ................ A61M 25/0054 |
| 2005/0124980 A1 | 6/2005 | Sanders |
| 2005/0137537 A1 | 6/2005 | Watson et al. |
| 2007/0112291 A1 | 5/2007 | Børgesen |
| 2010/0030196 A1 | 2/2010 | Hildebrand et al. |
| 2012/0087869 A1 * | 4/2012 | Thakker ............... A61K 31/711 424/9.34 |
| 2014/0343500 A1 * | 11/2014 | Fielder ............. A61M 39/0247 604/288.01 |
| 2016/0089521 A1 | 3/2016 | Dragoon et al. |
| 2017/0325685 A1 | 11/2017 | Shachar et al. |
| 2018/0117243 A1 | 5/2018 | Maguire |
| 2019/0009014 A1 | 1/2019 | Chen et al. |
| 2019/0184139 A1 | 6/2019 | Nelson et al. |
| 2019/0269850 A1 | 9/2019 | Shih et al. |
| 2020/0061362 A1 | 2/2020 | Singh et al. |

FOREIGN PATENT DOCUMENTS

| | | |
|---|---|---|
| WO | WO2012138854 A1 | 10/2012 |
| WO | WO2013134486 A4 | 9/2013 |
| WO | WO2016059162 A1 | 4/2016 |
| WO | WO2020046791 A1 | 3/2020 |

* cited by examiner

| | |
|---|---|
| 300 | IMPLANT A DEEP BRAIN CATHETER WITHIN THE BRAIN OF A PATIENT SO THAT THE DISTAL END IS IMPLANTED WITHIN A DEEP BRAIN STRUCTURE OF THE PATIENT AND THE PROXIMAL END IS POSITIONED WITHIN THE SUBARACHNOID SPACE DIRECTLY ADJACENT TO THE BRAIN. |
| 302 | IMPLANT AN INTRATHECAL DRUG DELIVERY DEVICE WITHIN THE TORSO OF THE PATIENT SO THAT INTRATHECAL DRUG DELIVERY DEVICE DELIVERS THE ONE OR MORE PHARMACEUTICAL AGENTS INTRATHECALLY TO THE CSF WITHIN THE SPINAL CANAL OF THE PATIENT |
| 304 | ADMINISTER ONE OR MORE PHARMACEUTICAL AGENTS INTRATHECALLY TO CSF WITHIN THE SPINAL CANAL SO THAT DIFFUSION AND PULSATE FLOW OF CSF TRANSPORTS THE PHARMACEUTICAL AGENT THROUGH THE DEEP BRAIN CATHETER FROM THE SUBARACHNOID SPACE TO THE DEEP BRAIN STRUCTURE |

FIG. 6

IMPLANTABLE MEDICAL DEVICE FOR DELIVERY OF PHARMACOLOGICAL AGENTS TO THE DEEP BRAIN STRUCTURES

TECHNICAL FIELD

The present disclosure relates generally to implantable medical devices, and more particularly implantable drug pumps or ports and delivery of pharmaceutical agents to the cerebrospinal fluid ("CSF").

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, drug infusion pumps, ports, or other fluid delivery devices can be used for chronic delivery of pharmaceutical agents. Typically, such devices provide therapy continuously or periodically according to programmed parameters. The programmed parameters can specify the therapeutic regimen (e.g., the rate, quantity, and timing of medicament delivery to a patient), as well as other functions of the medical device. Additionally, or alternatively, delivery of pharmaceutical agents may be provided by bolus (e.g., periodic) injections aided by the use of infusion pumps or ports or other implantable devices that provide access to key positions within a patient's body such as the cerebrospinal fluid.

Implantable drug infusion pumps or ports can provide important advantages over other forms of medicament administration. For example, oral administration is often difficult because the systematic dose of the substance needed to achieve the therapeutic dose at the target site may be too large for the patient to tolerate without adverse side effects. Also, some substances simply cannot be absorbed in the stomach adequately for a therapeutic dose to reach the target site. Moreover, substances needed in the brain that are not lipid-soluble may not cross the blood-brain barrier adequately if taken via oral administration. Implantable drug pumps or ports can also help avoid the problem of patient noncompliance, viz. the patient failing to take the prescribed drug or therapy as instructed.

Implantable drug pumps or ports are typically implanted at a location within the body of a patient (typically a subcutaneous region in the lower abdomen) and are configured to deliver a fluid medicament through a catheter to a target treatment site. Drug pumps typically include a pumping mechanism that delivers the pharmaceutical agent to the patient under a set schedule over an extended period of time, while drug ports typically receive bolus injections and then deliver the pharmaceutical agent to the target treatment site. The catheter used in these devices is generally configured as a flexible tube with a lumen running the length of the catheter that transports the pharmaceutical agent from the drug pump or drug port to a target treatment site within the patient's body.

SUMMARY

Embodiments of the present disclosure include a system and method configured to provide intrathecal drug delivery with improved accessibility to deep brain structures of a patient. The present disclosure provides an approach that uses an intrathecal drug delivery device, such as a drug pump or drug port, in conjunction with introducing a deep brain catheter within the patient's brain to create a fluid pathway between the deep brain structure and the subarachnoid space adjacent the brain (e.g., within the subcranial space, as opposed to the neck or torso areas). The system delivers the pharmaceutical agent intrathecally to the CSF within the spinal canal and relies on diffusion and the natural pulsatile flow of the CSF to transport and deliver the pharmaceutical agent to the target deep brain structure through the deep brain catheter. The deep brain catheter acts as an artificial perivascular pathway but, due to the comparatively larger lumen diameter of the catheter versus the perivascular pathways within the brain, the deep brain catheter provides a much more efficient and accessible fluid pathway for reaching the targeted deep brain structures.

In an embodiment, the disclosure describes an intrathecal drug delivery system including an intrathecal drug delivery device configured to deliver a fluid including one or more pharmaceutical agents intrathecally to a cerebrospinal fluid (CSF) within a spinal canal of a patient. The system further includes a deep brain catheter including an elongated body extending from a proximal end to a distal end and defining an inner lumen, where the distal end is configured to be implanted within a deep brain structure of the patient and the proximal end is configured to be positioned within the subarachnoid space directly adjacent to the brain to provide a passageway via the inner lumen between subarachnoid space and the deep structure. The drug delivery system being configured to transport the pharmaceutical agent using diffusion, pulsatile flow of the CSF, or both through the deep brain catheter from the subarachnoid space to the deep brain structure.

In another embodiment, the disclosure describes a method for treating a medical condition including providing a deep brain catheter having an elongated body extending from a proximal end to a distal end and defining an inner lumen, where the deep brain catheter is implanted so that the distal end is implanted within a deep brain structure of the patient and the proximal end is positioned within the subarachnoid space directly adjacent to the brain. The method also including administering one or more pharmaceutical agents using a intrathecal drug delivery to a cerebrospinal fluid (CSF) within a spinal canal of a patient so that diffusion and pulsatile flow of the CSF transports the pharmaceutical agent through the deep brain catheter from the subarachnoid space to the deep brain structure.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which:

FIG. 6 is a flow diagram of a method of implanting and using the disclosed intrathecal drug delivery system for the treatment of one or more medical conditions.

Figure 1A:
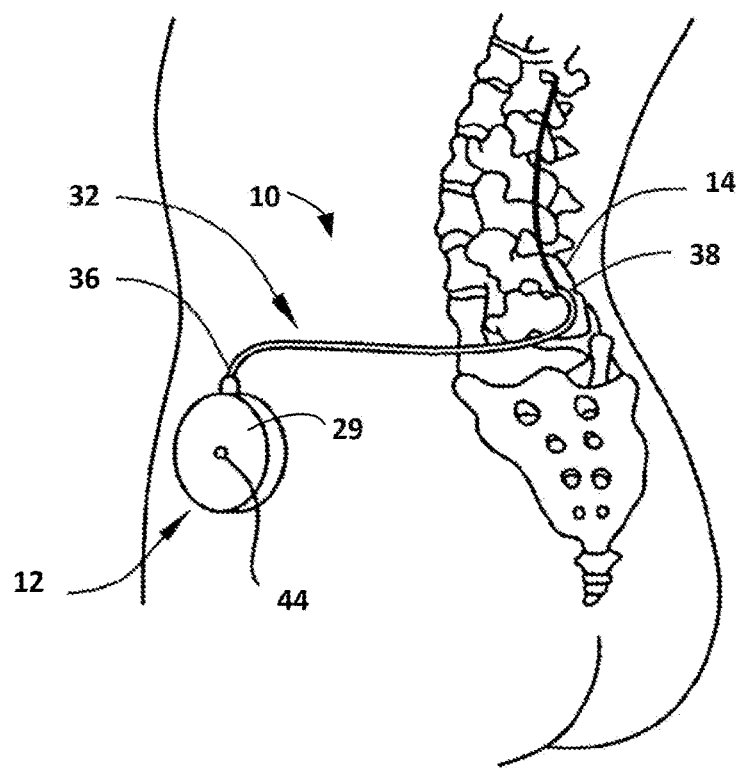
FIG. 1A is a schematic diagram of a portion of an intrathecal drug delivery system that includes an intrathecal drug delivery device implanted within the body of a patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Previous attempts of drug delivery to deep brain structures within the brain have faced several challenges. For example, one approach for drug delivery to the brain has included using an implantable infusion pump with a long delivery catheter having a distal end directly positioned within the brain tissue for direct access and delivery of pharmaceutical agents to a targeted deep brain structure. However, these systems require a rather invasive approach to implant the infusion pump within the body of the patient (typically near the clavicle or abdomen) and tunnel the delivery catheter along the patient's spine and neck and through the cranium into the brain tissue to the target deep structure. In addition to the invasiveness of this approach, such catheter assemblies may suffer from migration due to the transitions through the neck and skull and active movement of the patient. Additionally, certain therapeutic agents may be incapable of direct delivery into the brain without adequate dilution of the pharmaceutical agent which may be challenging or difficult to obtain with a direct delivery regimen.

An alternative approach to direct infusion to the brain includes using an infusion pump or port mounted within the abdomen of a patient that delivers pharmaceutical agents directly to CSF within the spinal canal of a patient. This approach offers a less invasive alternative that relies on the indirect delivery of the pharmaceutical agent to the brain by delivering the agent to the CSF and relying on diffusion of the pharmaceutical agent within the CSF to reach the brain. However, in such examples, it may be difficult for the pharmaceutical agent to access targeted structures deep within the brain tissue, may require a higher drug load to reach an effective dosage, and the like. The present disclosure may address one or more of the above problems by providing a less invasive approach than intracranial infusion pumps, for example, by providing a system that indirectly delivers pharmaceutical agents to the brain via the CSF to reach targeted deep structures.

Figure 1B:
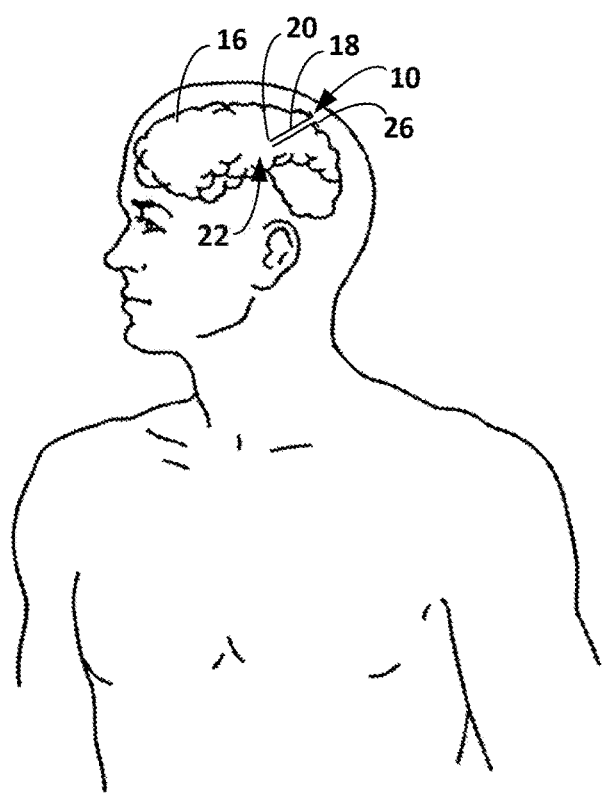
FIG. 1B is a schematic diagram of another portion of the intrathecal drug delivery system of FIG. 1A that includes a deep brain catheter spanning between a targeted deep brain structure and the subarachnoid space.

FIGS. 1A and 1B are schematic diagrams collectively showing an intrathecal drug delivery system 10 for introducing pharmaceutical agents to the deep structures of the brain. FIG. 1A shows the lower abdomen of the patient and an intrathecal drug delivery device 12 for infusing a fluid containing one or more pharmaceutical agents into CSF 28 (FIG. 2) within the spinal canal 14 of the patient. FIG. 1B shows the head and brain 16 of the patient with deep brain catheter 18 implanted within brain 16 such that the distal end 20 of deep brain catheter 18 is positioned adjacent to a targeted deep brain structure 22 (e.g., a structure below the pia mater of the brain and physically separated from the subarachnoid space 24 in FIG. 2) and a proximal end 26 positioned within subarachnoid space 24 adjacent to brain 16 (e.g., within the subcarinal space). Although depicted in connection with a human body, it should be understood that the drug delivery systems of the present disclosure could also be used on non-human animals.

Drug delivery device 12 works in conjunction with deep brain catheter 18 to deliver the pharmaceutical agents contained within drug delivery device 12 to deep brain structure 22 by relying on the passive diffusion and pulsatile flow of CSF 28 to transport the agents to subarachnoid space 24 of brain 16. As described further below, drug delivery device 12 includes a drug reservoir 30 (FIG. 3) housing a fluid containing one or more pharmaceutical agents. Drug delivery device 12 then delivers the fluid, via intrathecal catheter 32, to the patient's CSF 28 within spinal canal 14, thereby avoiding the need to tunnel catheter 32 through the neck or cranium of the patient.

Figure 2:
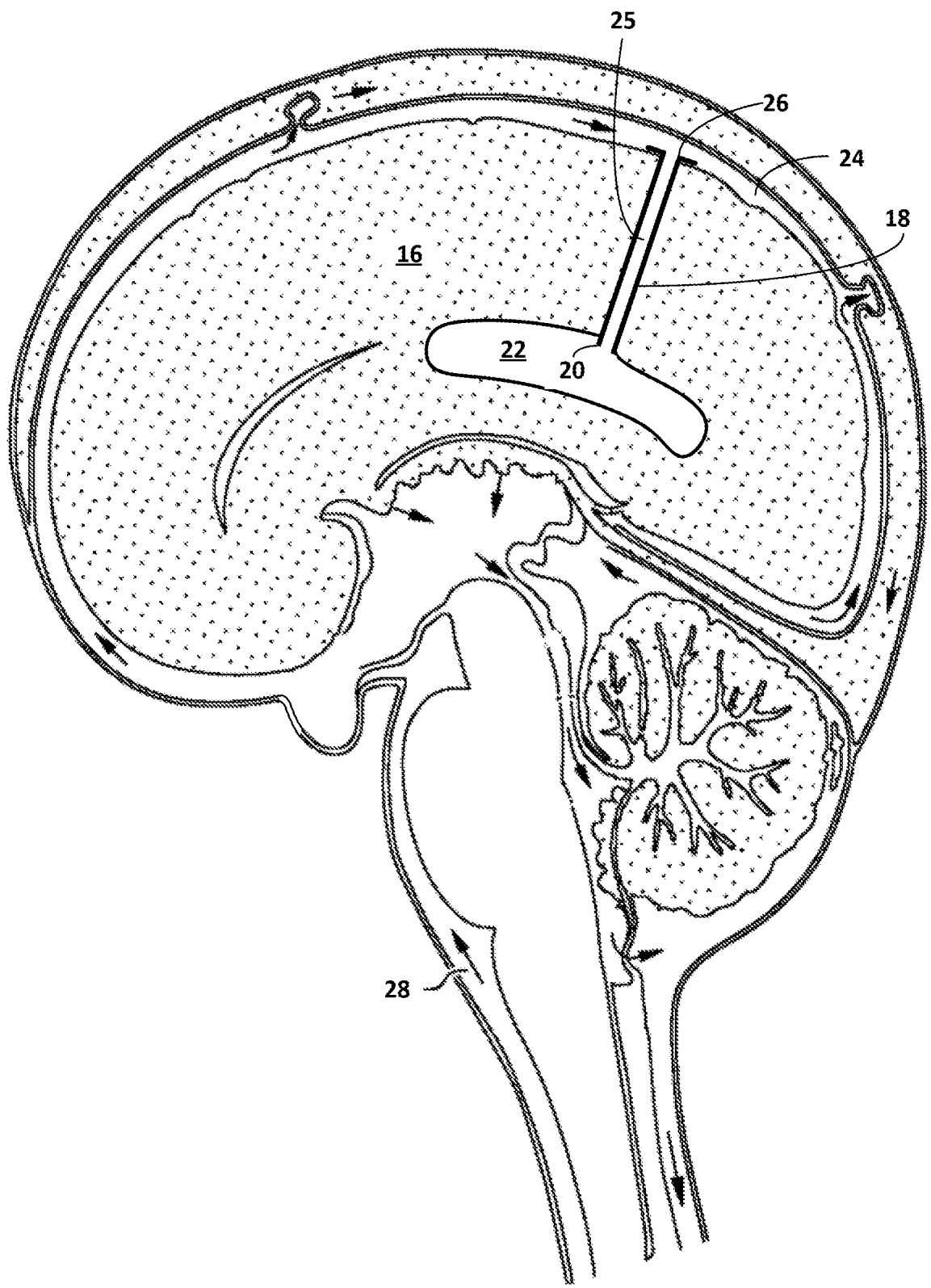
FIG. 2 is a cross-sectional view of a patient's brain, a set of associated spaces containing cerebrospinal fluid, the flow of cerebrospinal fluid in such spaces, and an example deep brain catheter connecting such spaces.

Referring to FIG. 2, once delivered to the CSF 28, the CSF containing the one or more pharmaceutical agents then exits the foramen of Magendie and Luschka to flow around the brainstem and cerebellum within subarachnoid space 24. CSF 28 is produced in the ventricular system of the brain and communicates freely with subarachnoid space 24 via the foramen of Magendie and Luschka, wherein the subarachnoid space 24 is a compartment within the central nervous system that contains CSF 28. The arrows within the subarachnoid space 24 in FIG. 2 indicate the flow of CSF 28.

The brain and spinal cord are surrounded by CSF 28, which provides a cushioning effect for the spinal cord, but also provides a vehicle to deliver substances such as proteins, glucose, and ions (e.g. sodium, calcium, and potassium) to the central nervous system. CSF 28 naturally moves around brain 16 under a pulsatile flow process and cleanses the brain. Generally, CSF 28 is transported along the perivascular spaces around brain arteries and veins to reach deep brain structures. However, these passages are highly restricted and may not allow for the successful penetration of the pharmaceutical agents to deep brain structures 22 leading to ineffective treatment, need for higher drug doses, or both. Deep brain catheter 18 acts as an artificial perivascular space for intracerebroventricular (ICV) or intraparenchymal (IPa) drug delivery of the pharmaceutical agents to deep brain structure 22. However, unlike intraparenchymal delivery systems (e.g., direct delivery to targeted deep brain tissue), the disclosed system relies on intrathecal drug delivery of the pharmaceutical agent, which helps dilute the agent within CSF 28 and avoid certain complications associated with direct tissue delivery while simultaneously improving the efficiency and reducing the drawbacks associated with traditional intrathecal drug delivery systems by using deep brain catheter 18 to increase access to deep brain structure 22 and improve delivery and efficacy.

Distal end 20 of deep brain catheter 18 may be introduced at an appropriate location adjacent to deep brain structure 22 for improved ICV, IPa, or similar drug delivery mechanism for the treatment of various medical conditions. While distal end 20 is shown with only a single opening, deep brain catheter 18 may include one or more distal openings to allow for efficient diffusion and delivery of the pharmaceutical agents within CSF 28 to the targeted deep brain structure. In some embodiments, distal end 20 may include a porous membrane or other structure to help diffuse the material passing through lumen 25 over a specified target area. Additionally, or alternatively, such openings may include one or more structures such as valves, membranes, or the like configured to maintain the openings within deep brain catheter 18 and prevent occlusion over time.

Deep brain catheter 18 may be constructed of any suitable material, e.g., an elastomeric tube. Examples of some suitable materials include, but are not limited to, silicone rubber (e.g., polydimethyl siloxane), polyurethane, parylene, PTFE, and the like depending on the desired treatment location. Preferably, deep brain catheter 18 is chemically inert such that it will not interact with drugs or body tissue or body fluids over a long time period.

Deep brain catheter 18 defines an inner lumen 25 having a diameter preferably large enough to allow CSF 28 to flow through inner lumen 25 under the natural pulsatile flow of the CSF. In some embodiments, inner lumen 25 may define a diameter of about 0.5 millimeters (mm) to about 2.5 mm and the wall thickness of catheter 18 may be about 0.5 mm to about 1 mm. The total length of deep brain catheter 18 may be about 10 mm to about 150 mm although other lengths may be used to allow for proper spanning between the subarachnoid space 24 adjacent brain 16 and deep brain structure 22.

Deep brain catheter 18 may be introduced into brain 16 using any suitable technique. In some embodiments, deep brain catheter 18 may be inserted using a guide member (e.g., wire, catheter, or stylet) through the patient's skull and into brain 16, whereupon the guide member is removed after placement of catheter 18. That introduction may be aided through the use of a stereotactic frame, a frameless stereotaxy procedure carried out manually (free hand) by the physician, or may be performed robotically or with robotic assistance. During insertion, the guide member may be aided by visual tracking techniques such as CT, MRI, or other means of accurately ascertaining and maintaining the location of the guide member or deep brain catheter 18. Deep brain catheter 18 may be implanted within brain 16 without the need to tunnel catheter 18 or include other devices through the neck of the patient. Further, once implanted, deep brain catheter 18 may be fully contained within the subcarinal space of the patient without the need for an access point through the cranium.

Distal end 20 of deep brain catheter 18 may be positioned adjacent various types of deep brain structures 22 for treating various medical conditions. Example deep brain structures 22 may include but are not limited to, the putamen, caudate, internal capsule, thalamus, subthalamic nucleus, striatum, globus pallidus, and the like. The particular deep brain structure 22 is not intended to be limited other than that the structure exists within the tissue of brain 16 below the pia mater that is otherwise not directly accessible via, or in contact with, the subarachnoid space 24 within the cranium.

Intrathecal drug delivery device 12 used in drug delivery system 10 may include any suitable device configured to deliver a fluid containing one or more pharmaceutical agents to CSF 28 within spinal canal 14 of a patient. For purposes of this disclosure, drug delivery device 12 is generally described as an implantable drug pump, which may optionally include a pumping mechanism and internal processing circuitry and power supply to deliver the pharmaceutical agent at a set rate or schedule, or as an implantable drug port that is configured to receive a bolus injection or infusion allowing for delivery into CSF 28. However other suitable devices may also be used in system 10 for the delivery of the pharmaceutical agent to CSF 28. Conventional drug pumps or ports are used for dispensing medication within the body. These devices both have drug reservoirs which can either be filled for dispensation on a time-release basis (such as with an implantable drug pump), or which allow for insertion of medication that is dispensed through an implantable catheter (such as with an access port). In both devices, the reservoir for receiving medication is commonly sealed with a pierceable septum. A hypodermic needle is inserted through the skin, the access port, and the septum and into the reservoir. Once within the reservoir, the medication is dispensed from the syringe into the drug reservoir.

Figure 3:
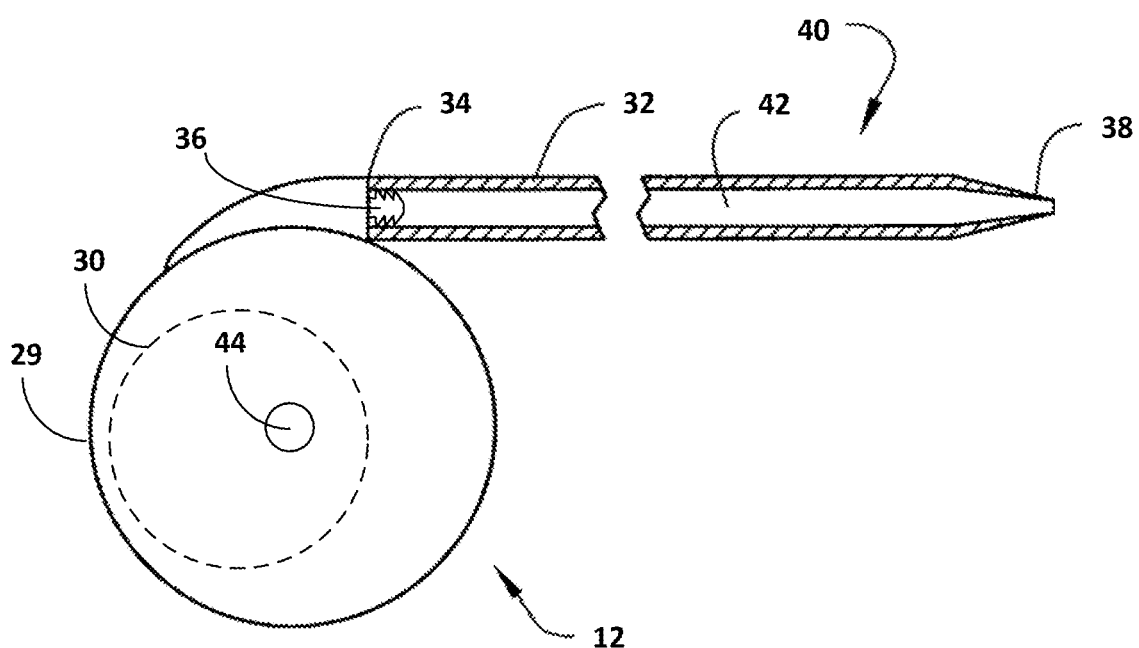
FIG. 3 is a schematic diagram of an implantable intrathecal drug delivery device that can be used with the intrathecal drug delivery system of FIG. 1A.

FIG. 3 shows an exemplary structure of a drug pump 29 that may be used as the drug delivery device 12 in drug delivery system 10 of FIG. 1A. Drug pump 29 is coupled to intrathecal catheter 32, which is shown in an enlarged half section. The size of intrathecal catheter 32 is exaggerated for ease of illustration of the structure thereof and the full length of intrathecal catheter 32 is not shown for simplicity of illustration.

Drug pump 29 includes a drug reservoir 30 housing one or more pharmaceutical agents that are delivered via intrathecal catheter 32 to CSF 28 of the patient within spinal canal 14. In some embodiments, drug pump 29 may further include an access port 44 disposed on an exterior of the housing with a self-sealing septum enabling a needle to access to drug reservoir 30 percutaneously. Port 44 may be used to refill drug reservoir 30 for the purpose of scheduled drug delivery. Examples of some suitable drug pumps may include, e.g., commercially available implantable infusion pumps such as the SYNCHROMED pumps, such as Models 8611H, EL 8626, and EL 8627, manufactured by Medtronic, Inc., Minneapolis, Minn. It should be understood that some pumps used in connection with the present disclosure may not require a separate power supply.

Figure 4:
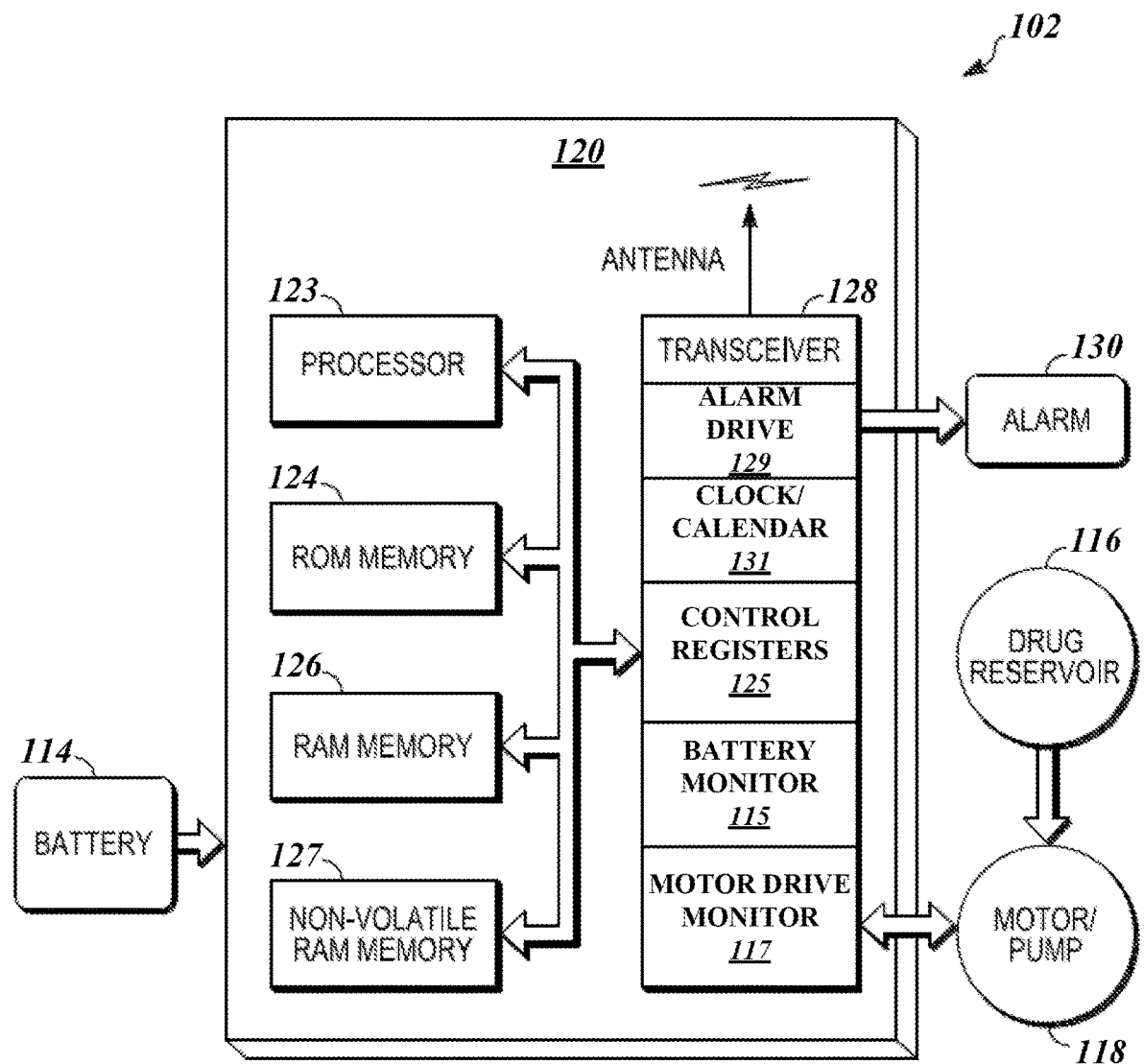
FIG. 4 is a schematic diagram of a drug delivery pump that may be used with the implantable intrathecal drug delivery system of FIG. 1A.

FIG. 4 shows a schematic diagram of an example drug pump 102, illustrating the various electronic components 120 of the device. As shown, drug pump 102 includes power source 114 and pump mechanism 118. Power source 114 can be a battery, such as a lithium-ion battery. The power source 114 can be carried in the housing of pump 102 and can operate medicament pump 118 and electronic components 120. A battery-monitoring device 115 can monitor a battery power of the battery 114, and a motor-drive monitor 117 can monitor operation of pump motor 118.

The electronic components 120 can include a processor 123, Read-Only Memory (ROM) 124, Random-Access Memory (RAM) 126, Non-volatile RAM 127, and transceiver circuitry 128 that can interface with one or more control registers 125. In one embodiment, the processor 124 can be an Application-Specific Integrated Circuit (ASIC) state machine, gate array, controller, microprocessor, CPU, or the like. The electronic components 120 can be generally configured to control infusion of medicament according to programmed parameters or a specified treatment protocol. The programmed parameters or specified treatment protocol can be stored in memory 126 or 127. Transceiver circuitry 128 can be configured to receive information from and transmit information to, the external programmer or server. In one embodiment, electronic components 120 can be further be configured to operate a number of other features, such as, for example, a patient alarm 130 operable with an internal clock and/or calendar 131 and an alarm drive 129.

Implantable medical pump 102 can be configured to receive programmed parameters and other updates from the external programmer, which can communicate with implantable medical pump 102 through well-known techniques such as wireless telemetry. In some embodiments, the external programmer can be configured for exclusive communication with one or more implantable medical pumps 102. In other embodiments, the external programmer can be any computing platform, such as a mobile phone or tablet. In some embodiments, implantable medical pump 102 and an external programmer can further be in communication with a cloud-based server. The server can be configured to receive, store and transmit information, such as program parameters, treatment protocols, drug libraries, and patient information, as well as data recorded by implantable medical pump 102. In some embodiments, pump 102 may provide tactile feedback to the user indicating the location of a needle as described in this disclosure.

Figure 5:
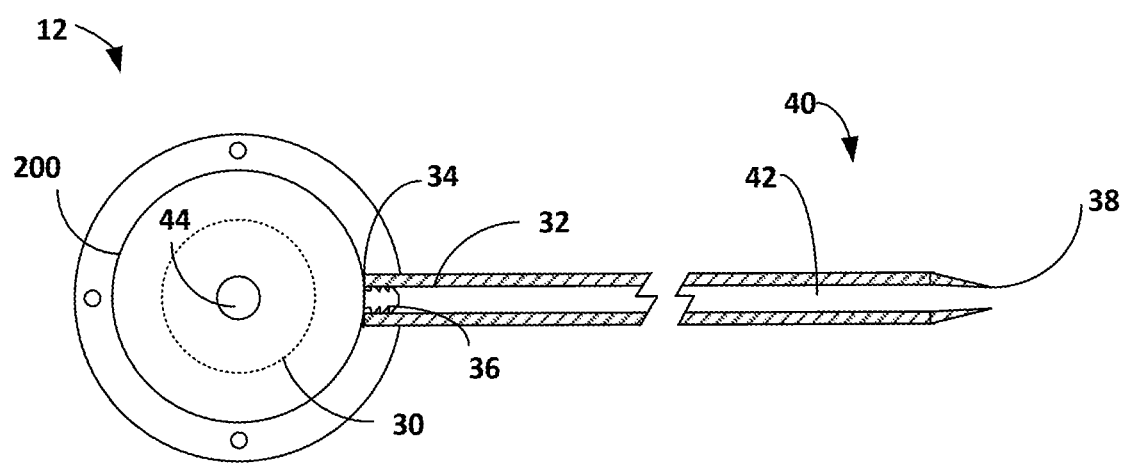
FIG. 5 is a schematic diagram of another implantable intrathecal drug delivery device that can be used with the intrathecal drug delivery system of FIG. 1A.

FIG. 5 is a schematic diagram of an example intrathecal drug port 200 that can be used as drug delivery device 12 of intrathecal drug delivery system 10 of FIG. 1A. As shown, drug port 200 may include a drug reservoir 30 accessible via access port 44. Drug port 200 is coupled to intrathecal catheter 32 to provide access to CSF 28 (FIG. 2). Drug reservoir 30 and access port 44 may be substantially similar to those components described above. However, in contrast to drug pump 29 of FIG. 3, drug port 200 lacks a pumping mechanism or processing circuitry and functions as a passive access point for delivering one or more pharmaceutical agents via a bolus injection or infusion to CSF 28.

The housing of drug pump 29 or drug port 200 can be constructed of a material that is biocompatible and hermetically sealed, such as titanium, tantalum, stainless steel, plastic, ceramic, or the like to protect the inner workings and components of drug pump 29 or port 200. Drug pump 29 or drug port 200 are preferably surgically implanted subcutaneously in the pectoral, abdominal, or lower-back region of the subject's body and configured using any suitable mechanism capable of delivering a fluid containing one or more pharmaceutical agents to CSF 28 within spinal canal 14 of the patient.

Both drug pump 29 and drug port 200 include an intrathecal catheter 32 having an elongated tubular portion 40 that extends from the proximal end 34 to the distal end 38 and defines an inner lumen 42. The proximal end 34 of intrathecal catheter 32 is coupled to drug pump 29 or port assembly 200 using a connector 36 and distal end 38 is implanted within the spinal canal 14. A drug delivered from drug reservoir 30 to the catheter 32 then passes through lumen 42 and exits the catheter through one or more openings at or near distal end 38. When implanted for delivering drugs to the spinal region, at least a portion of catheter 32 is located within intrathecally within CSF 28 of the patient such that as drug exits the catheter 32 and enters directly into the CSF so the pharmaceutical agent does not contact other tissues or bodily fluids before reaching CSF 28 of the patient. Intrathecal catheter 32 is distinct and independent of deep brain catheter 18 of FIG. 1B, and is not intended to have the distal end 38 implanted within the head of the patient.

The body of catheter 32 may be constructed of any suitable material, e.g., an elastomeric tube. When implanted in spinal canal 14, intrathecal catheter 32 may be floating free in CSF 28 and may contact the spinal cord of the patient. As a result, intrathecal catheter 32 may preferably be soft and flexible to limit any chance of damaging the spinal cord. Examples of some suitable materials include, but are not limited to, silicone rubber (e.g., polydimethyl siloxane) or polyurethane, both of which can provide good mechanical properties and are very flexible. Suitable materials for intrathecal catheter 32 are also preferably chemically inert such that they will not interact with drugs or body tissue or body fluids over a long time period.

The inside diameter, e.g., the diameter of the lumen 42 of intrathecal catheter 32, is preferably large enough to accommodate expected infusion rates with acceptable flow resistance for delivery of the pharmaceutical agent to CSF 28 as known by those in the art. As an example, intrathecal catheter 32 may have an outside diameter of about 1 mm to about 2 mm and an inside diameter of about 0.4 mm to about 0.8 mm. In some embodiments, intrathecal catheter 32 may be about 5 centimeters (cm) to about 50 cm long to reach from, e.g., drug pump 29 or drug port 200 implanted in the patient's abdomen to the spine.

The disclosed drug delivery system 10 may be used to treat various neurological diseases; examples are chronic pain, tremors, Parkinson's disease, epilepsy, or other brain disorders. Various types of pharmaceutical agents may be used for the treatment of such diseases. In some examples, Gabapentin, Baclofen, Midazolam, Valproate Na, or combinations thereof may be administered to CSF 28 for the treatment of epilepsy. Suitable daily does for Gabapentin may include between about 0.1 mg and about 200 mg for the treatment. Baclofen may be administered at a daily dose of between about 50 μg/day and about 1500 μg/day. Midazolam may be administered directly to a patient's CSF 28 at any daily dose of between about 0.1 mg/day and about 5 mg/day. Valproate Na may be administered directly to a patient's CSF 28 at a daily dose of between about 5 mg/day and about 100 mg/day. It will be understood that daily dose requirements may be adjusted to account for variability in CSF volume, CSF production rates, and rates of clearance of Gabapentin from the CSF. One of skill in the art will understand that such variability may be due in part to, e.g., gender and/or age.

FIG. 6 is a flow diagram of a method of implanting and using intrathecal drug delivery system 10 for the treatment of one or more medical conditions. The method depicted in FIG. 6 includes: implanting deep brain catheter 18 within brain 16 of a patient so that distal end 20 is implanted within deep brain structure 22 and proximal end 26 is positioned within subarachnoid space 24 directly adjacent to the brain 16 (300); implanting intrathecal drug delivery device 12 within the torso (e.g., abdomen, lower back, or chest) of the patient so that device 12 delivers the one or more pharmaceutical agents intrathecally to CSF 28 within spinal canal 14 of the patient (302); and administering one or more pharmaceutical agents intrathecally to CSF 28 within spinal canal 14 so that diffusion and pulsatile flow of CSF 28 transports the one or more pharmaceutical agents through deep brain catheter 18 from subarachnoid space 24 to deep brain structure 22 (304).

As discussed above, implanting deep brain catheter 18 within brain 16 (300) can be performed using any suitable technique such as one or more of the procedures typical for hydrocephalus shunt implantation, intracerebroventricular (ICV) or intraparenchymal (IPa) catheter implantation, neurostimulation, or the like. Deep brain catheter 18 allows for the fluidic connection between deep brain structure 22 and subarachnoid space 24 containing CSF and the one or more pharmaceutical agents without needing to tunnel a catheter through the neck and cranium of the patient or directly connect to delivery device 12.

The method of FIG. 6 includes implanting intrathecal drug delivery device 12 within the torso patient (302) using any suitable technique. In preferred arrangements, the drug pump 29 or drug port 300 will be implanted within the abdomen, lower back, or chest area of the patient. Intrathecal catheter 32 may be tunneled using appropriate means such that the distal end 38 of catheter 32 is positioned in the CSF within spinal canal 14 of the patient and proximal end 34 is coupled to drug pump 29 or port 200 (e.g., coupled via connector 36).

While implantation of intrathecal drug delivery device 12 is generally described as being part of the implantation and treatment process of system 10, it will be understood that the disclosed system can also rely on previously implanted intrathecal drug delivery devices. For example, existing patients with drug delivery devices 12 implanted for the treatment of one or more medical conditions may gain a benefit by the subsequent introduction of deep brain catheter 18. In such patients, the improved access to deep brain structures 22 via catheter 18 may allow for the previously implanted drug delivery device 12 to be reprogramed to reduce the concentration of pharmaceutical agent being administered, reduce the daily dosage of the pharmaceutical agent delivered, or both. In some examples, reduction of pharmaceutical agents being delivered due to the including of deep brain catheter 18 may help reduce the likelihood of drug side effects and or increase the duration between clinical visits necessary to refill drug reservoir 30 without reducing the efficacy of treatment.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An intrathecal drug delivery system comprising:
   an intrathecal drug delivery device to intrathecally diffuse a pharmaceutical agent into a cerebrospinal fluid (CSF) within a spinal canal of a patient; and
   a deep brain catheter comprising an elongated body extending from a proximal end to a distal end and defining an inner lumen, wherein when the system is implanted in the patient, the distal end is implanted within a deep brain structure of the patient and the proximal end is positioned within a subarachnoid space directly adjacent to a brain of the patient to provide a fluid passageway between the subarachnoid space and the deep brain structure,
   wherein the proximal end of the deep brain catheter is not coupled to the intrathecal drug delivery device; and
   wherein the drug delivery system relies only on a natural pulsatile flow of the CSF to transport the pharmaceutical agent from the spinal canal to the subarachnoid space, through the deep brain catheter, and to the deep brain structure.

2. The intrathecal drug delivery system of claim 1, wherein when the system is implanted in the patient, the intrathecal drug delivery device comprises:
   a drug reservoir to receive the pharmaceutical; and
   an intrathecal catheter comprising a first end coupled to the intrathecal drug delivery device and a second end implanted within the spinal canal of the patient to deliver the pharmaceutical agent from the drug reservoir to the CSF, wherein the second end of the intrathecal catheter is not coupled to the proximal end of the deep brain catheter.

3. The intrathecal drug delivery system of claim 2, wherein the intrathecal drug delivery device comprises a drug pump comprising:
   a pump mechanism to pump the pharmaceutical agent from the drug reservoir through the intrathecal catheter into the CSF continuously at a predetermined flow rate or periodically according to a delivery schedule;
   an exterior housing defining an access port; and
   a self-sealing septum disposed across the access port, wherein the self-sealing septum can provide a needle with access to the drug reservoir percutaneously.

4. The intrathecal drug delivery system of claim 2, wherein the intrathecal drug delivery device comprises a drug port comprising:
   an exterior housing defining an access port; and
   a self-sealing septum disposed across the access port, wherein the self-sealing septum can provide a needle with access to the drug reservoir percutaneously.

5. The intrathecal drug delivery system of claim 1, wherein the distal end of the deep brain catheter comprises one or more openings to release the pharmaceutical agent diffused within the CSF into the deep brain structure.

6. The intrathecal drug delivery system of claim 1, wherein the deep brain catheter defines an overall length of greater than about 10 millimeters (mm).

7. The intrathecal drug delivery system of claim 6, wherein the deep brain catheter defines an overall length of less than about 150 mm.

8. The intrathecal drug delivery system of claim 1, wherein the deep brain catheter defines an inner lumen diameter of greater than about 0.5 millimeters (mm).

9. The intrathecal drug delivery system of claim 8, wherein the deep brain catheter defines an inner lumen diameter of less than 2.5 mm.

10. A method for treating a medical condition, the method comprising:
   implanting a distal end of a deep brain catheter within a deep brain structure of a patient and a proximal end of the deep brain catheter within a subarachnoid space directly adjacent to a brain of the patient; and
   diffusing, via an intrathecal drug delivery device that is not coupled to the deep brain catheter, a pharmaceutical agent into a cerebrospinal fluid (CSF) within a spinal canal of the patient such that a natural pulsatile flow of the CSF transports the pharmaceutical agent from the spinal canal to the subarachnoid space through the deep brain catheter, and to the deep brain structure.

11. The method of claim 10, further comprising implanting the intrathecal drug delivery device within a torso of the patient.

12. The method of claim 11, wherein the intrathecal drug delivery device comprises:
   a drug reservoir to receive the pharmaceutical agent; and
   an intrathecal catheter having a first end connected to the drug delivery device and a second end positioned in the CSF within the spinal canal of the patient to facilitate transport of the pharmaceutical agent from the drug reservoir to the CSF, wherein the second end of the intrathecal catheter is not coupled to the proximal end of the deep brain catheter.

13. The method of claim 10, wherein the pharmaceutical agent treats chronic pain, epilepsy, tremors, or a brain disorder of the patient.

14. The method of claim 10, wherein the deep brain catheter defines an overall length of greater than about 10 millimeters (mm).

15. The method of claim 14, wherein the deep brain catheter defines an overall length of less than about 150 mm.

16. The method of claim 10, wherein the deep brain catheter defines an inner lumen diameter of greater than about 0.5 millimeters (mm).

17. The method of claim 16, wherein the deep brain catheter defines an inner lumen diameter of less than 2.5 mm.

18. The method of claim 10, wherein implanting the distal end and the proximal end of the deep brain catheter comprises implanting the deep brain catheter entirely within a cranium of the patient, and physically separate from the intrathecal drug delivery device.

19. The intrathecal drug delivery system of claim 1, wherein the deep brain catheter is insertable into the brain using a guide member.

20. The intrathecal drug delivery system of claim 19, wherein the guide member is removable after placement of the catheter, such that, once implanted, the deep brain catheter is fully contained within the subcranial space without the need for an access point.

* * * * *